US011366822B2

(12) United States Patent
Lee et al.

(10) Patent No.: US 11,366,822 B2
(45) Date of Patent: Jun. 21, 2022

(54) METHOD, APPARATUS AND COMPUTER PROGRAM FOR MAPPING MEDICAL DATA

(71) Applicant: UNIVERSITY-INDUSTRY COOPERATION GROUP OF KYUNG HEE UNIVERSITY, Gyeonggi-do (KR)

(72) Inventors: Sung Young Lee, Gyeonggi-do (KR); Ali Taqdir, Gyeonggi-do (KR)

(73) Assignee: UNIVERSITY-INDUSTRY COOPERATION GROUP OF KYUNG HEE UNIVERSITY, Gyeonggi-Do (KR)

( * ) Notice: Subject to any disclaimer, the term of this patent is extended or adjusted under 35 U.S.C. 154(b) by 451 days.

(21) Appl. No.: 16/348,127

(22) PCT Filed: Nov. 7, 2017

(86) PCT No.: PCT/KR2017/012524
§ 371 (c)(1),
(2) Date: May 7, 2019

(87) PCT Pub. No.: WO2018/084682
PCT Pub. Date: May 11, 2018

(65) Prior Publication Data
US 2019/0361908 A1    Nov. 28, 2019

(30) Foreign Application Priority Data

Nov. 7, 2016 (KR) .......................... 10-2016-0147459

(51) Int. Cl.
*G06F 16/25* (2019.01)
*G16H 50/70* (2018.01)
(Continued)

(52) U.S. Cl.
CPC ............ *G06F 16/258* (2019.01); *G16H 50/70* (2018.01); *G16H 10/60* (2018.01); *G16H 50/20* (2018.01)

(58) Field of Classification Search
USPC ......................................................... 705/2–3
See application file for complete search history.

(56) References Cited

U.S. PATENT DOCUMENTS 8,229,881 B2 * 7/2012 Pedro .................... G06F 16/367
707/600
8,620,931 B2 * 12/2013 Zillner .................... G06N 5/02
707/749

(Continued)

FOREIGN PATENT DOCUMENTS

JP    2011520195    7/2011
JP    2015524107    8/2015

(Continued)

OTHER PUBLICATIONS

Kim, et al., "Clinical MetaData ontology: a simple classification scheme for data elements of clinical data based on semantics", BMC Medical Informatics and Decision Making, pp. 1-11, 2019 (Year: 2019).*

(Continued)

*Primary Examiner* — Amber A Misiaszek
(74) *Attorney, Agent, or Firm* — Adsero IP

(57) ABSTRACT

The present invention relates to a method for mapping heterogeneous medical data, the method comprising the steps of: generating domain clinic model ontology that defines a concept of arbitrary medical data collected from individual clinics and a relationship between the medical data; if SNOMED CT ontology that defines the concept and relationship of the domain clinic model ontology and standardized medical terms is loaded and the concept included in the domain clinic model ontology and/or the SNOMED (Continued)

CT ontology has a degree of similarity equal to or greater than a preset threshold value, determining that the concept has been mapped and generating a DCM-SNOMED mapping file for the mapping information; if vMR ontology describing the concept and relationship of data models defined by the SNOMED CT ontology and Health Level 7 standard is loaded and the concept included in the SNOMED CT ontology and/or the vMR ontology has a degree of similarity equal to or greater than a preset threshold value, determining that the concept has been mapped and generating a vMR-SNOMED mapping file for the mapping information; and generating a DCM-vMR mapping file for mapping information between the arbitrary medical data collected from the individual clinics and the concept included in the vMR ontology by using the DCM-SNOMED mapping file and the MR-SNOMED mapping file.

6 Claims, 2 Drawing Sheets

(51) Int. Cl.
 *G16H 10/60* (2018.01)
 *G16H 50/20* (2018.01)

(56) References Cited

U.S. PATENT DOCUMENTS

| | | | | |
|---|---|---|---|---|
| 2008/0201280 | A1* | 8/2008 | Martin | G16H 30/20 706/45 |
| 2011/0093481 | A1* | 4/2011 | Hussam | G16H 10/20 707/756 |
| 2012/0110016 | A1* | 5/2012 | Phillips | G06F 16/285 707/E17.014 |
| 2013/0086069 | A1* | 4/2013 | Phillips | G06F 16/285 707/737 |
| 2015/0149191 | A1* | 5/2015 | Lee | G06F 40/30 705/2 |
| 2015/0356270 | A1* | 12/2015 | Devarakonda | G16H 15/00 705/3 |

FOREIGN PATENT DOCUMENTS

| | | |
|---|---|---|
| KR | 10-2011-0108998 | 10/2011 |
| KR | 10-2015-0061456 | 6/2015 |
| KR | 10-2015-0061457 | 6/2015 |
| KR | 10-2015-0073569 | 7/2015 |
| KR | 10-1878217 | 7/2018 |

OTHER PUBLICATIONS

Ali et al., "Semantic Reconciliation Model for interoperable and shareable knowledge authoring environment", Beyond AlphaGo, Oct. 27-28, 2016, International Symposium on Perception, Action and Cognitive Systems, 1 page.

International Search Report for PCT/KR2017/012524 dated Mar. 20, 2018, 5 pages (including the English translation).

Office Action for KR10-2016-0147459, dated Dec. 19, 2017, 7 pages (in Korean language).

Fujita et al., "SNOMED-CT & ICD-11 Ready to Use Ontology", Journal of the Japanese Society for Artificial Intelligence, vol. 25, No. 4 (2010), with English abstract.

Office Action for Japanese Application No. 2019-523636, dated Jun. 1, 2020, with English translation, 6 pages.

Ontology, Chapter 7, National Clinical Database, with English abstract, 41 pages.

* cited by examiner

METHOD, APPARATUS AND COMPUTER PROGRAM FOR MAPPING MEDICAL DATA

CROSS-REFERENCE TO RELATED APPLICATION

This application claims priority to and is a 35 U.S.C. § 371 national phase application of PCT/KR2017/012524 (WO2018/084682), filed on Nov. 7, 2017 entitled "METHOD, APPARATUS AND COMPUTER PROGRAM FOR MAPPING MEDICAL DATA", which application claims priority to and the benefit of Korea Patent Application No. 10-2016-0147459, filed Nov. 7, 2016, the disclosures of which are incorporated herein by reference in their entirety.

TECHNICAL FIELD

The disclosure relates to a method for providing a mapping algorithm associated with heterogeneous terms and/or data forms to be applied to heterogeneous systems used in hospitals.

More particularly, the disclosure relates to a method of mapping domain clinical model data which is used by an individual clinic to SNOMED CT which is substantially used as a reference in the medical field, mapping the SNOMED CT to a vMR format that is used in the Health Level 7 data model standard, and eventually mapping the DCM data to the vMR.

BACKGROUND ART

Various terms associated with patients' data from various locations need to be standardized to enable all hospitals to apply the terms to all systems, whereby many hospitals can smoothly use multiple support systems.

To this end, conventionally, SNOMED CT is substantially used as a reference associated with medical terms, and vMR defined by the Health Level 7 standard defines a standard format of medical data.

Health Level 7 (hereinafter referred to as HL7) is certified by the American National Standard Institute (ANSI) which a standard institute that provides standards of various domains such that various pieces of information from the software applications of different health and medical treatment fields can be compatible with each other, and is one of the standards for electronically exchanging medical information.

However, currently, individual clinics use medical terms and/or data in different forms. Particularly, there are various local terms used in the clinics. In one hospital, local terms may be different for each doctor and for each department.

Therefore, medical data are not utilized well. When a patient changes hospital, when a hospital changes a system to a different system, or when a patient is transferred from a first department to a second department, existing medical information may not be used since medical terms and/or data formats are different, which is a drawback.

DETAILED DESCRIPTION OF THE INVENTION

Technical Problem

Therefore, the disclosure has been made to solve the above-mentioned problem. An aspect of the disclosure is to provide a mapping algorithm associated with heterogeneous terms and/or data forms to be applied to heterogeneous systems used in hospitals.

Technical Solution

In accordance with an aspect of the disclosure, a method of mapping heterogeneous medical data includes: an operation configured to generate a domain clinic model ontology that defines concepts of medical data collected from an individual clinic and relations between the medical data; an operation configured to load the domain clinic model ontology and an SNOMED CT ontology that defines concepts and relations of standardized medical terms, when concepts included in the domain clinic model ontology and/or SNOMED CT ontology have a similarity greater than or equal to a predetermined threshold value, to determine that the corresponding concepts are mapped, and to generate a DCM-SNOMED mapping file associated with the mapping information; an operation configured to load the SNOMED CT ontology and a vMR ontology that describes concepts and relations of data models defined in the Health Level 7 standard, when concepts included in the SNOMED CT ontology and/or the vMR ontology have a similarity greater than or equal to a predetermined threshold value, to determine that the corresponding concepts are mapped, and to generate a vMR-SNOMED mapping file associated with the mapping information; and an operation configured to generate a DCM-vMR mapping file associated with mapping information between the medical data collected from the individual clinic and the concepts included in the vMR ontology, using the DCM-SNOMED mapping file and the MR-SNOMED mapping file.

In accordance with another aspect of the disclosure, a method of mapping heterogeneous medical data includes: loading a domain clinic model ontology that defines concepts of medical data collected from an individual clinic and relations between the medical data, and an SNOMED CT ontology that defines concepts and relations of standardized medical terms, and calculating a similarity of concepts included in the domain clinic model ontology and/or the SNOMED CT ontology; loading the SNOMED CT ontology and a vMR ontology that describes concepts and relations of data models defined in the Health Level 7 standard, and performing natural language processing on concepts included in the SNOMED CT ontology and/or the vMR ontology so as to calculate a similarity of concepts between the ontologies; and calculating mapping information between concepts included in the domain clinic model ontology and/or the vMR ontology.

In accordance with another aspect of the disclosure, a system for mapping heterogeneous medical data includes: a domain clinic model ontology that defines concepts of medical data collected from an individual clinic and relations between the medical data; an SNOMED CT ontology that defines concepts and relations of standardized medical terms; a vMR ontology that describes concepts and relations of data models defined by the Health Level 7 standard; an automatic mapping authentication module configured to load the domain clinic model ontology and the SNOMED CT ontology, when concepts included in the domain clinic model ontology and/or the SNOMED CT ontology have a similarity greater than or equal to a predetermined threshold value, to determine that the corresponding concepts are mapped, and to generate a DCM-SNOMED mapping file associated with the mapping information; a category mapping module configured to load the SNOMED CT ontology and the vMR ontology, when concepts included in the SNOMTED CT ontology and/or the vMR ontology have a similarity greater than or equal to a predetermined threshold value, to determine that the corresponding concepts are mapped, and to generate a vMR-SNOMED mapping file associated with the mapping information; and a reconciliation and inference module configured to generate a mapping file associated with mapping information between the medical data collected from the individual clinic and the concepts included in the vMR ontology, using the DCM-SNOMED mapping file and the MR-SNOMED mapping file.

In accordance with another aspect of the disclosure, an apparatus for mapping heterogeneous medical data includes: a domain clinic model ontology that defines concepts of medical data collected from an individual clinic and relations between the medical data; an SNOMED CT ontology that defines concepts and relations of standardized medical terms; a vMR ontology that describes concepts and relations of data models defined by the Health Level 7 standard; an automatic mapping authentication module configured to generate a mapping file associated with the domain clinic model ontology and the SNOMED CT ontology; a category mapping module configured to generate a mapping file associated with the SNOMED CT ontology and the vMR ontology; and a reconciliation and inference module configured to generate a mapping file associated with mapping information between the medical data collected from the individual clinic and the concepts included in the vMR ontology, using the DCM-SNOMED mapping file and the vMR-SNOMED mapping file.

In accordance with another aspect of the disclosure, an apparatus for mapping heterogeneous medical data includes: a domain clinic model ontology that defines concepts of medical data collected from an individual clinic and relations between the medical data; an SNOMED CT ontology that defines concepts and relations of standardized medical terms; a vMR ontology that describes concepts and relations of data models defined by the Health Level 7 standard; a first module configured to load the domain clinic model ontology and the SNOMED CT ontology, and to calculate a similarity of concepts included in the domain clinic model ontology and/or the SNOMED CT ontology; a second module configured to load the SNOMED CT ontology and the vMR ontology, and to perform natural language processing on concepts included in the SNOMED CT ontology and/or the vMR ontology, so as to calculate a similarity of concepts between the ontologies; and a third module configured to calculate mapping information between concepts included in the domain clinic model ontology and/or the vMR ontology.

In accordance with another aspect of the disclosure, there is provided a server according to an embodiment, wherein a computer program that is recorded in a computer readable recording medium so as to implement mapping of heterogeneous medical data performs: a function of loading a domain clinic model ontology that defines concepts of medical data collected from an individual clinic and relations between the medical data; a function of loading an SNOMED CT ontology that defines concepts and relations of standardized medical terms; a function of loading a vMR ontology that describes concepts and relations of data models defined in the Health Level 7 standard; a function of determining that concepts are mapped when the corresponding concepts included in the domain clinic model ontology and/or the SNOMED CT ontology have a similarity greater than or equal to a predetermined threshold value, and of generating a DCM-SNOMED mapping file associated with the mapping information; a function of determining that concepts are mapped when the corresponding concepts included in the SNOMED CT ontology and/or the vMR ontology have a similarity greater than or equal to a predetermined threshold value, and of generating a vMR-SNOMED mapping file; and a function of generating mapping information between the medical data collected from the individual clinic and the concepts included in the vMR ontology, using the DCM-SNOMED mapping file and the MR-SNOMED mapping file.

In accordance with another aspect of the disclosure, there is provided a server, wherein a computer program that is recorded in a computer readable recording medium so as to implement mapping of heterogeneous medical data performs: a function of loading a domain clinic model ontology that defines concepts of medical data collected from an individual clinic and relations between the medical data; a function of loading an SNOMED CT ontology that defines concepts and relations of standardized medical terms; a function of loading a vMR ontology that describes concepts and relations of data models defined in the Health Level 7 standard; a function of generating a mapping file associated with the domain clinic model ontology and the SNOMED CT ontology; a function of generating a mapping file associated with the SNOMED CT ontology and the vMR ontology; and a function of generating mapping information between the medical data collected from the individual clinic and the concepts included in the vMR ontology, using the DCM-SNOMED mapping file and the MR-SNOMED mapping file.

In accordance with another aspect of the disclosure, there is provided a server, wherein a computer program that is recorded in a computer readable recording medium so as to implement mapping of heterogeneous medical data performs: a function of loading a domain clinic model ontology that defines concepts of medical data collected from an individual clinic and relations between the medical data; a function of loading an SNOMED CT ontology that defines concepts and relations of standardized medical terms; a function of loading a vMR ontology that describes concepts and relations of data models defined in the Health Level 7 standard; a function of calculating a similarity of concepts included in the domain clinic model ontology and/or the SNOMED CT ontology; a function of performing natural language processing on concepts included in the SNOMED CT ontology and the vMR ontology so as to calculate a similarity of concepts included in both ontologies; and a function of calculating mapping information between the concepts included in the domain clinic model ontology and/or the vMR ontology.

Advantageous Effects

According to the disclosure, all medical data may be applied to clinic systems which are different for each location and each hospital, whereby medical contents may be utilized conveniently.

MODE FOR CARRYING OUT THE INVENTION

Figure 1:
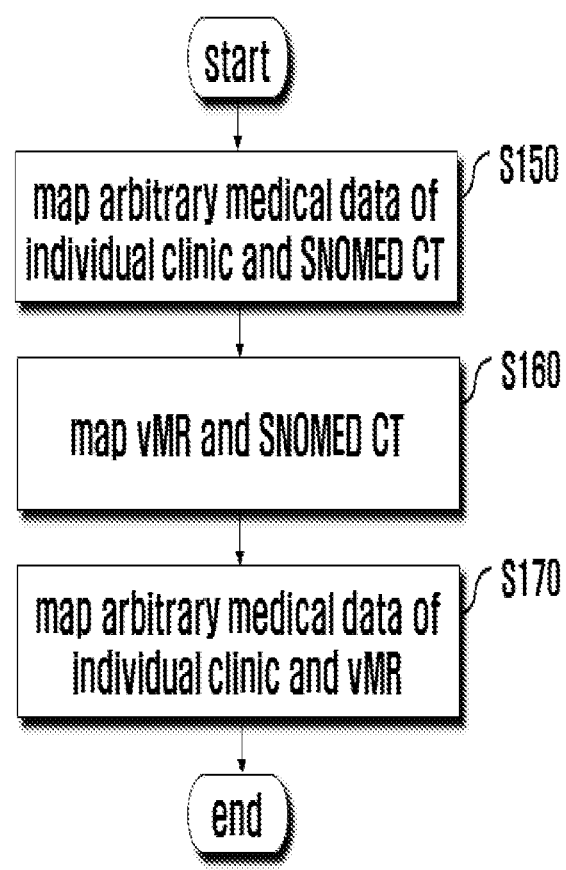
FIG. 1 is a flowchart illustrating a process of mapping heterogeneous medical data according to an embodiment of the disclosure.

The disclosure is not limited to the embodiments to be described below, and it is apparent that various modifications may be made without departing from the technical subject matter of the disclosure. Also, a description of a technology, which is well-known in the art and is not directly related to the technical subject matter of the disclosure, will be omitted.

In the drawings, like reference numerals denote like elements. In the drawings, some elements may be exaggerated, omitted, or schematically illustrated. Unnecessary descriptions which are not related to the subject matter of the disclosure are omitted in order to clearly describe the subject matter of the disclosure.

Most medical terms conventionally used are in the form of foreign languages or Chinese characters, and many terms are used to indicate one concept. Furthermore, medical data in the systems of hospitals are written in formats different for each database supplier, and thus, there is difficulty in communicating on the basis of information.

To solve the problem, standardization of medical terms and/or data has been attempted internationally. However, standardization that includes existing heterogeneous terms and existing heterogeneous data formats has not been implemented.

For example, the standardized term for the disease called "cecitis" is "appendicitis". However, depending on the situation, the disease is referred to as "cecitis", "appendicitis", "epityphlitis", or the like, and individual clinics may use all the terms together. The medical systems used by individual clinics are established in heterogeneous formats which are not unified. An individual clinic may use the commonly known standard format such as HL7 when storing electronic medical records. However, this is not compellable, and individual clinics may use different data formats. Actually, many individual clinics use unique data formats and styles, which is the chief impediment to exchanging information between clinics.

In order to solve the above-described problems, embodiments of the disclosure provide a method of mapping a medical data set used in an individual clinic to an SNOMED CT database which is substantially used as the standard reference of medical terms, mapping the SNOMED CT database to a vMR database defined by the Health Level 7 standard, and eventually mapping the DCM of the local clinic to vMR.

FIG. 1 is a flowchart illustrating a method of mapping medical data according to an embodiment of the disclosure. A medical data mapping system according to an embodiment of the disclosure may map a medical data set of an individual clinic to SNOMED CT in operation 150.

More particularly, the mapping system may map the medical data set of the individual clinic on the basis of an SNOMED CT ontology. To this end, the mapping system may provide a matching library.

The matching library may provide a plurality of mapping algorithms such as a string matching algorithm, a synonym matching algorithm, a label matching algorithm (synonym matching algorism), a structure-based child algorithm (child based structure algorithm), a structure-based property algorithm (property based structure algorithm), and the like. If it is determined that terms have a similarity within a predetermined threshold value according to the algorithms, it is considered that they are matched to one another.

More particularly, the string matching algorithm extracts similar concepts on the basis of matching between strings. The synonym matching algorithm may search a word net for a synonym having a meaning similar to that of a corresponding concept.

In addition, the label matching algorithm may match similar concepts using labels of concepts in a source concept ontology and a target concept ontology. The structure-based child algorithm employs source ontology concepts and target ontology concepts, and determines whether a child node of the source and a child node of the target match. Furthermore, the structure-based property algorithm may match similar concepts between source ontology concepts and target ontology concepts on the basis of the string matching algorithm.

The mapping system according to an embodiment may execute the algorithm, and may extract concepts obtained by mapping medical terms used in an individual clinic and standardized medical terms provided by the SNOMED CT ontology, so as to generate a mapping file. In the disclosure, this is referred to as DCM-SNOMED mapping.

The medical data mapping system according to an embodiment may map SNOMED CT and vMR in operation 160.

To this end, the medical data mapping system according to an embodiment may identify classification information from vMR specifications included in the vMR ontology, and may extract definitions of terms together with the classification information.

Furthermore, the medical data mapping system may identify classification information of the standardized medical terms provided from the SNOMED CT ontology, and may extract the definitions of the terms together with the classification information.

Subsequently, the mapping system may perform natural language processing of the terms extracted from the SNOMED CT and vMR, together with the classification information, and may perform processing of text including the corresponding terms.

The mapping system may apply an algorithm so as to calculate a similarity of terms between the SNOMED CT and the vMR. When the similarity of terms is greater than a predetermined threshold value, it is considered that the corresponding terms are mapped to each other.

The concepts of the mapped terms may be extracted from the SNOMED CT and the vMR, together with the classification information, and a mapping file may be generated. In the disclosure, this is referred to as vMR-SNOMED CT mapping.

Furthermore, the medical data mapping system according to an embodiment may perform DCM-vMR mapping using the DCM-SNOMED mapping and the vMR-SNOMED CT mapping, in operation 170.

More particularly, the medical data mapping system may load the DCM ontology first, and may extract medical terms from the DCM ontology.

The medical data mapping system may scan a DCM-SNOMED mapping document and a vMR-SNOMED CT mapping document which are produced in advance in operations 150 and 160.

The medical data mapping system identifies the concepts included in the documents while scanning the mapping documents, and when a predetermined concept is included in both documents, a DCM concept and a vMR concept corresponding thereto may be mapped to each other. In this manner, the medical data mapping system according to an embodiment may perform DCM-vMR mapping.

Figure 2:
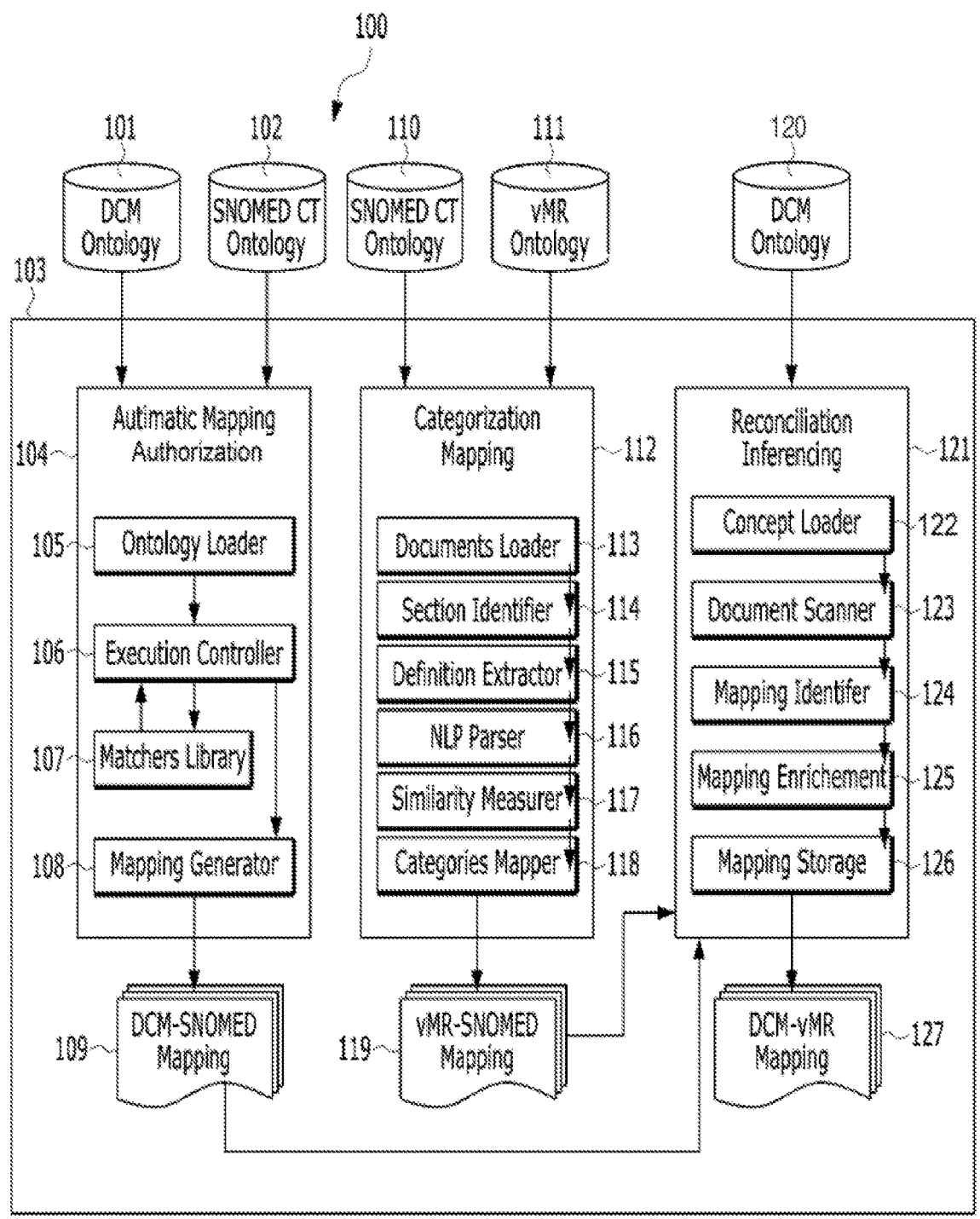
FIG. 2 is a block diagram illustrating the internal configuration of a module that maps heterogeneous medical data according to an embodiment of the disclosure.

FIG. 2 is a block diagram illustrating the operational configuration of a platform 103 that maps heterogeneous medical data according to an embodiment.

The medical data mapping system according to an embodiment may require a DCM ontology 101, an SNOMED CT ontology 102, and a vMR ontology as input values as illustrated in FIG. 2.

An ontology is a data model that describes a predetermined domain, and may include a set of formal terms that describes relations between concepts included in the predetermined domain. The ontology is used to clearly define and specifically describe the concept of a resource which is an object of an information system, so as to enable a user to obtain more accurate information, and may use languages such as RDF, OWL, SWRL, and the like in order to connect knowledge concepts from the perspective of meanings.

The DCM ontology 101 according to an embodiment may be a data model that describes the concepts and relations of medical terms collected from respective individual institutes.

The SNOMED CT ontology according to an embodiment may be a data model that describes the concepts and relations of standardized medical terms provided by the SNOMED CT.

The vMR ontology according to an embodiment may be a data model that describes the concepts and relations of data models provided by the vMR defined in the Health Level 7 standard.

As illustrated in FIG. 2, the medical data mapping platform may include an automatic mapping authorization module 104, a category mapping module 112, and an adjustment and inference module 121.

The automatic mapping authorization module 104 according to an embodiment may load the DCM ontology 101 and the SNOMED CT ontology 102, may analyze the concepts and relations between the ontologies, and may generate a DCM-SNOMED mapping file 109 associated with concepts that match between the ontologies.

Particularly, the data mapping system according to an embodiment may execute an ontology loader 105 of FIG. 2, so as to load the DCM ontology 101 and the SNOMED CT ontology 102.

The matching controller 106 may call a matching library 107 in order to determine whether concepts included in both ontologies match.

The matching library 107 may provide a plurality of mapping algorithms such as a string matching algorithm, a synonym matching algorithm, a label matching algorithm (synonym matching algorism), a structure-based child algorithm (child based structure algorithm), a structure-based property algorithm (property based structure algorithm), and the like. If it is determined that terms have a similarity within a predetermined threshold value using the algorithms, it is considered that they are matched to each other. More particularly, the string matching algorithm extracts similar concepts on the basis of matching between strings. The synonym matching algorithm may search a word net for a synonym having a meaning similar to that of a corresponding concept.

In addition, the label matching algorithm may match similar concepts using labels of concepts in a source concept ontology and a target concept ontology. The structure-based child algorithm employs the concepts of a source ontology and a target ontology, and determines whether a child node of the source and a child node of the target match. Furthermore, the structure-based property algorithm may match similar concepts between source ontology concepts and target ontology concepts on the basis of the string matching algorithm.

The matching controller 106 calls the matching library 107 so as to determine a similarity of concepts and relations included in both ontologies, and determines that corresponding concepts are matched when the similarity is greater than or equal to a predetermined threshold value, and a mapping generator 108 may generate the DCM-SNOMED mapping file 109 associated with the matched concepts and relations of the concepts.

The category mapping module 112 according to an embodiment may load the SNOMED CT ontology 110 and the vMR ontology 111 as illustrated in FIG. 2, may analyze concepts and relations between the ontologies, and may generate a vMR-SNOMED mapping file 119 associated with the concepts that match between both ontologies.

Particularly, the data mapping system according to an embodiment may execute a document loader 113 of FIG. 2, so as to load the DCM ontology 101 and the SNOMED CT ontology 102.

Subsequently, a section identifier 114 may identify classification information from vMR specifications included in the vMR ontology, and may identify the classification information of the standardized medical terms provided by the SNOMED CT ontology.

Furthermore, the definition extractor 115 may extract the vMR specifications included in the vMR ontology and the definitions of terms included in the SNOMED CT ontology.

A natural language parser 116 may perform natural language processing of extracted terms, together with classification information, and a similarity measurer 117 may calculate a similarity between processed terms by applying an algorithm. When the similarity is greater than or equal to a predetermined threshold value, a category mapper 118 may determine that the corresponding terms are mapped to each other, whereby the vMR-SNOMED CT mapping file 119 may be generated.

The reconciliation and inference module 121 according to an embodiment may load the DCM ontology 120 as illustrated in FIG. 2, and may eventually generate a DCM-vMR mapping file 127 using the DCM-SNOMED mapping file and the vMR-SNOMED mapping file.

More particularly, a concept loader 122 may extract medical terms from the DCM ontology as illustrated in FIG. 2.

A document scanner 123 may scan a DCM-SNOMED mapping document and a vMR-SNOMED CT mapping document which are generated in advance by the automatic mapping authorization module 104 and the category mapping module 112.

A mapping identifier 124 may identify the concepts included in the scanned documents, and when a predetermined concept is included in both documents, a DCM concept and a vMR concept corresponding thereto may be mapped to each other. In the same manner, a mapper 125 may generate the DCM-vMR mapping file 127, and may store the same in a mapping storage 126.

Embodiments of the disclosure provided in the present specification and the accompanying drawings are just predetermined examples for easily describing the technical contents of the disclosure and helping understanding of disclosure, but the disclosure is not limited thereto. It is apparent to those skilled in the technical field of the disclosure that other modifications based on the technical idea of the disclosure are possible.

The invention claimed is:

1. A method of mapping heterogeneous medical data, the method comprising:
    a step A of generating a domain clinic model ontology that defines one or more first concepts of medical data collected from an individual clinic and one or more first relations between the medical data;
    a step B of loading the domain clinic model ontology and an SNOMED CT ontology that defines one or more second concepts and one or more second relations of standardized medical terms, when the one or more first concepts and the one or more second concepts included in the domain clinic model ontology and SNOMED CT ontology have a first similarity greater than or equal to a first predetermined threshold value, determining that the corresponding concepts having the first similarity greater than or equal to the first predetermined threshold value are mapped, and generating a DCM-SNOMED mapping file associated with the mapping information;
    a step C of loading the SNOMED CT ontology and a vMR ontology that describes a format of one or more third concepts and third relations of data models in the Health Level 7 standard, when the one or more second concepts and the one or more third concepts included in the SNOMED CT ontology and the vMR ontology have a second similarity greater than or equal to a second predetermined threshold value, determining that the corresponding concepts having the second similarity greater than or equal to the second predetermined threshold value are mapped, and generating a vMR-SNOMED mapping file associated with the mapping information; and
    a step D of generating a DCM-vMR mapping file associated with mapping information between the one or more first concepts collected from the individual clinic and the one or more third concepts included in the vMR ontology, using the DCM-SNOMED mapping file and the vMR-SNOMED mapping file.

2. The method of claim 1, wherein the step B further comprises:
    calling a library for determining the first similarity of the one or more first concepts and the one or more second concepts included in the domain clinic model ontology and the SNOMED CT ontology,
    wherein the library comprises at least one of a string matching algorithm, a synonym matching algorithm, a label matching algorithm, a structure-based child algorithm (child based structure algorithm), and a structure-based property algorithm (property based structure algorithm).

3. The method of claim 2, wherein the step D further comprises:
    scanning the DCM-SNOMED mapping file and vMR-SNOMED mapping file so as to determine whether a predetermined concept is included in both files, and mapping the corresponding predetermined concept.

4. A method of mapping heterogeneous medical data, the method comprising:
    loading a domain clinic model ontology that defines one or more first concepts of medical data collected from an individual clinic and one or more first relations between the medical data, and an SNOMED CT ontology that defines one or more second concepts and one or more second relations of standardized medical terms, and calculating a first similarity of the one or more first concepts and the one or more second concepts included in the domain clinic model ontology and the SNOMED CT ontology;
    loading the SNOMED CT ontology and a vMR ontology that describes a format of one or more third concepts and one or more third relations of data models in the Health Level 7 standard, and performing natural language processing of the one or more second concepts and the one or more third concepts included in the SNOMED CT ontology and the vMR ontology so as to calculate a second similarity of the one or more second concepts and the one or more third concepts between the SNOMED CT ontology and the vMR ontology; and
    calculating mapping information between the one or more first concepts and the one or more third concepts included in the domain clinic model ontology and the vMR ontology based on the first similarity of the one or more first concepts and the one or more second concepts included in the domain clinic model ontology and the SNOMED CT ontology and the second similarity of the one or more second concepts and the one or more third concepts between the SNOMED CT ontology and the vMR ontology.

5. A system for mapping heterogeneous medical data, the system comprising:
    at least one processor; and
    a non-transitory computer readable medium communicatively coupled to the at least one processor, the non-transitory computer readable medium having stored thereon computer software comprising a set of instructions that, when executed by the at least one processor, causes the system to:
    receive a domain clinic model ontology that defines one or more first concepts of medical data collected from an individual clinic and one or more first relations between the medical data;
    receive an SNOMED CT ontology that defines one or more second concepts and one or more second relations of standardized medical terms;
    receive a vMR ontology that describes a format of one or more third concepts and one or more third relations of data models defined by the Health Level 7 standard;
    load the domain clinic model ontology and the SNOMED CT ontology, when the one or more first concepts and the one or more second concepts included in the domain clinic model ontology and the SNOMED CT ontology have a first similarity greater than or equal to a first predetermined threshold value, determine that the corresponding one or more first concepts and one or more third concepts are mapped, and generate a DCM-SNOMED mapping file associated with the mapping information;
    load the SNOMED CT ontology and the vMR ontology, when the one or more second concepts and the one or more third concepts included in the SNOMED CT ontology and the vMR ontology have a second similarity greater than or equal to a second predetermined threshold value, determine that the corresponding one or more second concepts and one or more third concepts are mapped, and generate a vMR-SNOMED mapping file associated with the mapping information; and
    generate a mapping file associated with mapping information between the one or more first concepts collected from the individual clinic and the one or more third concepts included in the vMR ontology, using the DCM-SNOMED mapping file and the vMR-SNOMED mapping file.

6. The system of claim 5, wherein the set of instructions, when executed by the at least one processor, further causes the system to:
load the domain clinic model ontology and the SNOMED CT ontology, and to calculate the first similarity of the one or more first concepts and the one or more second concepts included in the domain clinic model ontology and the SNOMED CT ontology;
load the SNOMED CT ontology and the vMR ontology, and to perform natural language processing of the one or more second concepts and the one or more third concepts included in the SNOMED CT ontology and the vMR ontology, so as to calculate the second similarity of the one or more second concepts and the one or more third concepts between the ontologies; and
calculate mapping information between the one or more first concepts and the one or more third concepts included in the domain clinic model ontology and the vMR ontology.

\* \* \* \* \*